United States Patent
de Juan, Jr.

(10) Patent No.: US 6,726,666 B2
(45) Date of Patent: *Apr. 27, 2004

(54) INLINE AIR HUMIDIFIER, A SYSTEM FOR HUMIDIFYING AIR AND METHODS RELATED THERETO

(75) Inventor: Eugene de Juan, Jr., Phoenix, MD (US)

(73) Assignee: The Johns Hopkins University, Baltimore, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/425,146

(22) Filed: Oct. 21, 1999

(65) Prior Publication Data

US 2002/0151872 A1 Oct. 17, 2002

Related U.S. Application Data

(62) Division of application No. 09/074,960, filed on May 7, 1998, now Pat. No. 5,997,498.

(51) Int. Cl.[7] .............................................. A61M 35/00
(52) U.S. Cl. ...................................................... 604/294
(58) Field of Search ................................ 604/290, 294, 604/291, 296; 128/200.11, 200.12, 200.13, 201.13, 204.15, 203.26; 165/140, 141, DIG. 10, DIG. 33; 261/DIG. 65

(56) References Cited

U.S. PATENT DOCUMENTS

| | | | | |
|---|---|---|---|---|
| 4,318,398 A | * | 3/1982 | Oetjen et al. | 128/201.13 |
| 4,327,717 A | * | 5/1982 | Oetjen et al. | 128/201.13 |
| 4,355,636 A | * | 10/1982 | Oetjen et al. | 128/204.13 |
| 4,550,713 A | | 11/1985 | Hyman | |
| 4,955,372 A | * | 9/1990 | Blackmer et al. | 128/203.16 |
| 5,042,468 A | | 8/1991 | Lambert | |
| 5,320,096 A | | 6/1994 | Hans | |
| 5,462,048 A | | 10/1995 | Lambert et al. | |
| 5,482,031 A | | 1/1996 | Lambert | |
| 5,651,783 A | | 7/1997 | Reynard | |
| 5,687,714 A | * | 11/1997 | Kolobow et al. | 128/207.14 |
| 5,733,572 A | | 3/1998 | Unger et al. | |
| 5,997,498 A | | 12/1999 | du Juan, Jr. | 604/26 |

OTHER PUBLICATIONS

Gibeck Product Literature.
Simms Portex Product Literature.

* cited by examiner

*Primary Examiner*—Manuel Mendez
(74) *Attorney, Agent, or Firm*—Peter F. Corless; Edwards & Angell, L.L.P.

(57) ABSTRACT

In preferred aspects the invention provides an in-line humidifier, a system using such a humidifier and methods related thereto, a method for infusing a gas into an eye during retinal detachment surgical procedure and a method for treating a retinal tear. The method for infusing gas includes providing an in-line humidifier, humidifying the gas in the in-line humidifier by flowing the gas there through and infusing the humidified gas into the eye. The in-line humidifier includes a housing and a humidifier section disposed within the housing, the humidifier section including a hydroscopic material that releasably retains liquid therein. The housing includes an inlet and outlet connection in fluid communication with the housing interior. The humidifier section is disposed within the housing so the gas entering through the inlet connection flows through the humidifying section, where small quantities of the releasably retinal liquid is released by the hydroscopic material to the flowing gas, and so the humidified gas exits the housing via the outlet connection.

10 Claims, 3 Drawing Sheets

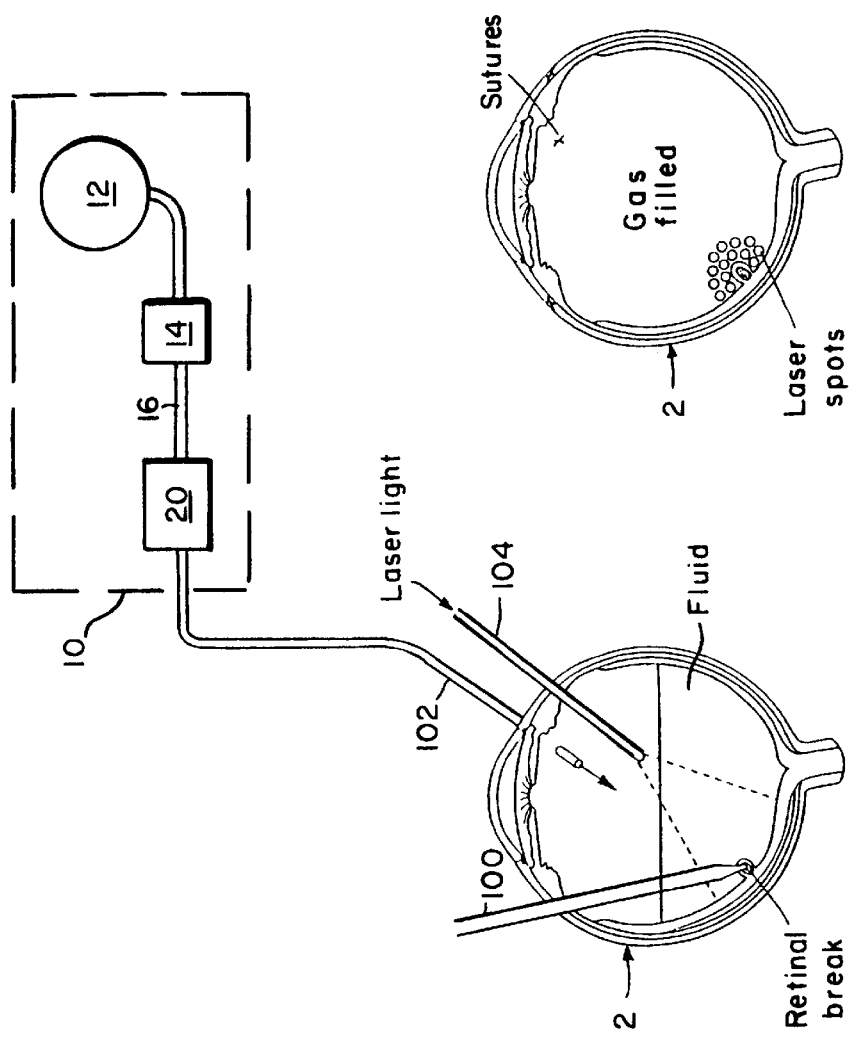
FIG.6C
FIG.6B
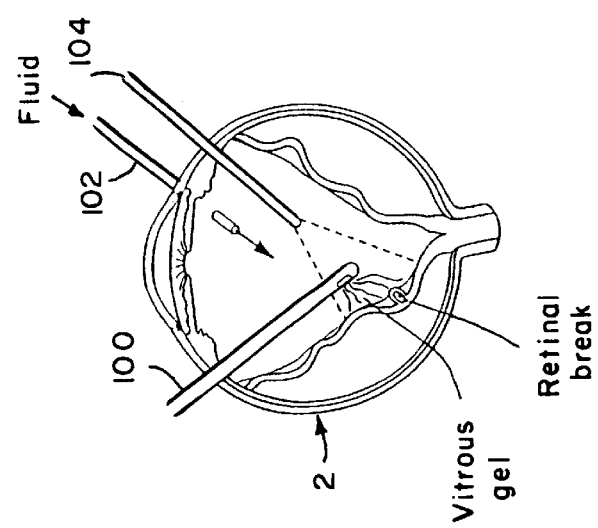
FIG.6A

INLINE AIR HUMIDIFIER, A SYSTEM FOR HUMIDIFYING AIR AND METHODS RELATED THERETO

This is a division of application Ser. No. 09/074,960 filed May 7, 1998, now U.S. Pat. No. 5,997,498.

FIELD OF THE INVENTION

The present invention relates to in-line air humidifiers and systems using such humidifiers, in particular to in-line humidifiers and systems using same in connection with medical procedures and techniques and more particularly to medical procedures and techniques involving the eye and eye surgery (e.g., retinal tear or detachment surgery).

BACKGROUND OF THE INVENTION

Retinal tears can occur when the vitreous, a clear gel-like substance that fills the centers of the eye, pulls away from the retina thereby leaving behind a tear or hole in the retina. Rhegmatogenous retinal detachments can result if the retinal breaks, i.e. tears or holes in the retina of an eye are not treated. With retinal breaks, fluid from the vitreous apparently seeps through the retinal break and accumulates under the retina. The degree of detachment is measured by the volume of subretinal fluid as well as the area of the retina involved. Some symptoms of retinal detachment include the presence of floaters, flashes, shadows or blind area, decreased visual acuity and metamorphopsia A number of techniques are employed for treating retinal detachments including using a scleral buckle, pneumatic retinopexy, cryopexy (i.e., freezing) and photocoagulation using a laser or xenon arc light source. These techniques may be used alone or in combination with each other to treat the retinal detachments for example, a combination of using a scleral buckle and photocoagulation. Additional retinal tears with little or no nearby detachment can be treated using photocoagulation or cryopexy.

In the photocoagulation technique when using a laser, the retinal break is surrounded with one or more rows of a plurality of laser burns or laser heat spots. These laser heat spots or burns produce scars, which prevents fluid from passing through and collecting under the retina. In the photocoagulation procedure, a gas is exchanged for the vitreous fluid being aspirated from within the eye so the gas is intraocular when performing photocoagulation. Typically, the gas is air from a tank that may be filtered and sterilized before it is infused into the eye.

Such air infusion of into the eye, however, can be quite problematic. For example, the infused air often can cause the lens of a patient's eye to become cloudy and dry, complicating the surgical procedure and creating conditions that can result in injury to the patient.

It thus would be desirable to have improved devices, systems and methods for infusing a gas, particularly air, to a patient's eye during eye surgery procedures. It would be particularly desirable to have improved devices, systems and methods for infusing air or other gas to a patient's eye during surgery wherein the eye lens remains substantially clear and moist.

SUMMARY OF THE INVENTION

We have now produced new devices and methods that enable infusing air or other gases into a patient's eye during surgical procedures whereby the eye remains quite clear and moist.

More particularly, the present invention provides a humidifier device and a system using such a humidifier, in particular a system configured for use in eye surgery, such as retinal tear and/or detachment surgery. The invention also provides related methods for humidifying air and infusing air during eye surgical procedures as well as a method for treating a retinal tear or detachment.

The methods of the invention in generally comprise providing a humidifier device, humidifying (i.e. adding moisture) to gas via the device and infusing the humidified gas to a patient's eye typically during an eye surgery procedure. The humidifier device is typically in-line, i.e. positioned in a gas flow path between the gas source and the patient's eye.

Preferred humidifier devices of the invention generally include a housing and a humidifying section disposed within the housing. The housing comprises an inlet and an outlet connection or port that fluidly communicates with the interior of the housing. The humidifying section is located within the housing so air entering the housing via the inlet connection passes through the humidifying section and thence out through the outlet connection, thereby humidifying the flowing air.

The humidifying section preferably includes material (preferably hydroscopic) that can be hydrated (e.g., initial charged with a liquid, such as a sterile saline solution) and selectively release moisture to the gas as it passes through the humidifying section. Preferably, the material also is a bacteriostatic material. Alternatively, the humidifying section is treated with a germicide or other agent. In general aspects, the humidifying section is any type of reservoir that allows for efficient humidification of the gas flowing therethrough. Also, in general aspects the hydroscopic material includes any one of a number of materials known in the art, including but not limited to cellulose, absorbent synthetic materials, papers including corrugated paper, and the like. Additionally, the humidifying section can have a variety of structural configurations and shapes including a cylinder that permits the passage of air between the inlet and outlet connections. In a particular embodiment, the humidifying section is a cylinder of concentric layers of corrugated paper or other absorbent material configured to maintain a desired shape and integrity of the air flow passage after the corrugated absorbent material has absorbed a desired quantity of liquid. Such a preferred cylinder design is suitably configured to allow the air to flow along the long axis of the cylindrical humidifying section.

The device housing may be suitably constructed of any one of a number of materials known in the art that is appropriate for the intended use including maintaining structural integrity while being exposed to the humidified air. More particularly, the housing is constructed of a plastic material such as a rigid polypropylene, polyethylene and the like. In a preferred embodiment, the housing includes a visual port or is constructed, at least in part, of a clear plastic material that allows a surgeon or other device user to observe the condition of the hydroscopic material of the humidifying section within the housing.

In one aspect of the invention, the device housing is constructed to form a one-piece structure in which is disposed the humidifying section. In another aspect of the invention the housing is constructed so as to have two or more members that are releasably secured to each so a single structure is formed when the humidifier is assembled for use.

A humidifying system of a device of the invention suitably will be in communication with a source of flowing gas (particularly air) and an in-line humidifier as described above. Such a system can further include an air filter that filters the air before it passes through the humidifier. In a more specific embodiment, the filter or system further includes the capability to sterilize the air. The system typically includes tubing that interconnects the various components that form the system. The source of air that flows through the system and is infused into a patient's eye suitably can be a commercially available pressurized tank of air or the like.

Other aspects and embodiments of the invention are discussed below.

BRIEF DESCRIPTION OF THE DRAWINGS

FIGS. 6A–C are cross-sectional schematic views of an eye undergoing a retinal tear repair procedure while using a humidifying system of the invention.

DETAILED DESCRIPTION OF THE INVENTION

Figure 1:
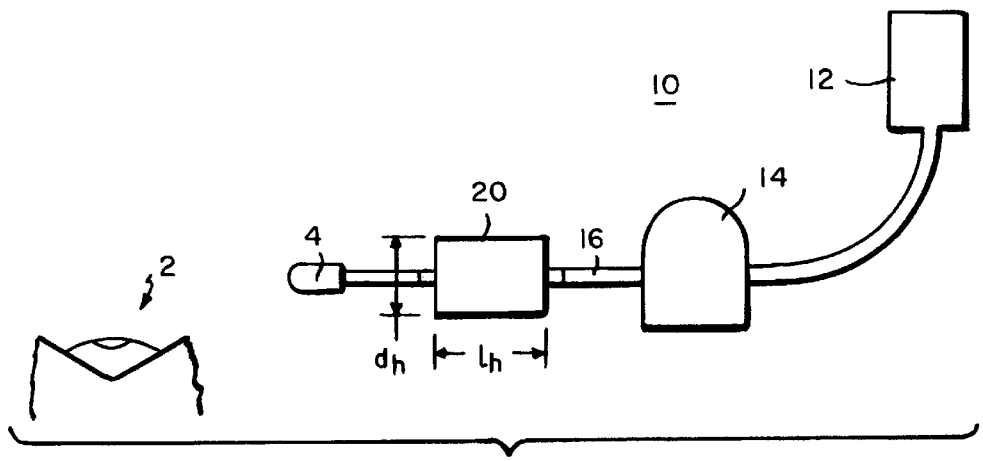
FIG. 1 is a schematic view of a humidification system according to the present invention.

Referring now to the various figures wherein like reference characters refer to like parts, FIG. 1 depicts a preferred system 10 for humidifying air according to the present invention in which air is infused into an eye 2 during, for example a retinal detachment surgical procedure. Although the illustrated system is for infusing air into the eye the system of the present invention is not limited to such a use. It is within the scope of the present invention for such a humidifying system to be used in conjunction with other medical procedures, particularly other surgical procedures involving the posterior segment of the eye and/or phakic fluid/gas exchange, particularly those involving prolonged infusion of a gas.

System 10 includes gas supply 12, filter 14, in-line humidifier 20 and interconnecting tubing 16. Gas from gas supply 12 (e.g. a pressurized air tank) is communicated by way of the interconnecting tubing 16 to the filter 14 and the filtered gas is communicated via the interconnecting tubing to in-line humidifier 20. The filtered and humidified gas is then communicated via the interconnecting tubing 16 to a surgical instrument, for example a gas inflow instrument 4 or cannula used in retinal detachment surgery that infuses air into an eye.

Although generally less preferred, devices of the invention may omit filter element 14. In such a design, gas from the gas supply 12 is communicated directly to the humidifier 20 by means of the interconnecting tubing 16.

The gas supply 12 in an illustrative embodiment is a pressure tank, however, the gas supply can be any of a number of means for storing and distributing a gas into a feed line including a pressure regulated gas supply system. Alternatively, the gas supply 12 can be the gas supply system of a facility or a structure in which the system is located. For example, the gas supply can be the compressed air system in a hospital or other medical facility. In an exemplary use, the gas supply 12 is a source of dry filtered air and more particularly a source of sterile, dry filtered air. The gas being supplied includes air, sulfur hexafluorine, perfluoro propane and any other gas known to those skilled in the art that can be infused into an eye. Typically, the gas is supplied at a pressure sufficient to maintain the shape of the eye without injury, for example between about 0 and 100 mm Hg or more particularly, between about 20–40 mm Hg.

Filter 14 filters the gas to remove particulate matter and infectious material such as bacteria in the micron and sub-micron range. The filter 14 also is preferably configured to sterilize the gas or air as it passes there through. In an exemplary embodiment, the filter 14 is a MILLEX-GS manufactured by the Millipore Corporation.

Figure 2:
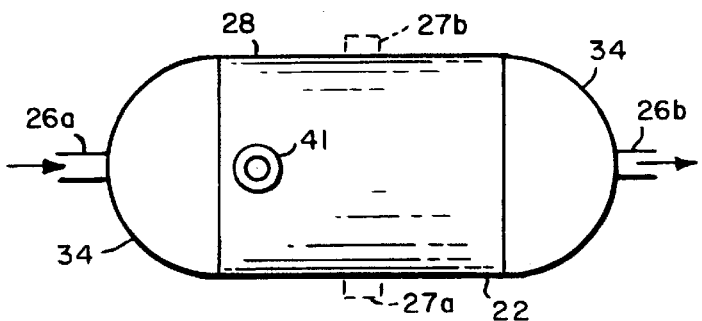
FIG. 2 is a side view of an in-fine humidifier according to the present invention.
Figure 3:
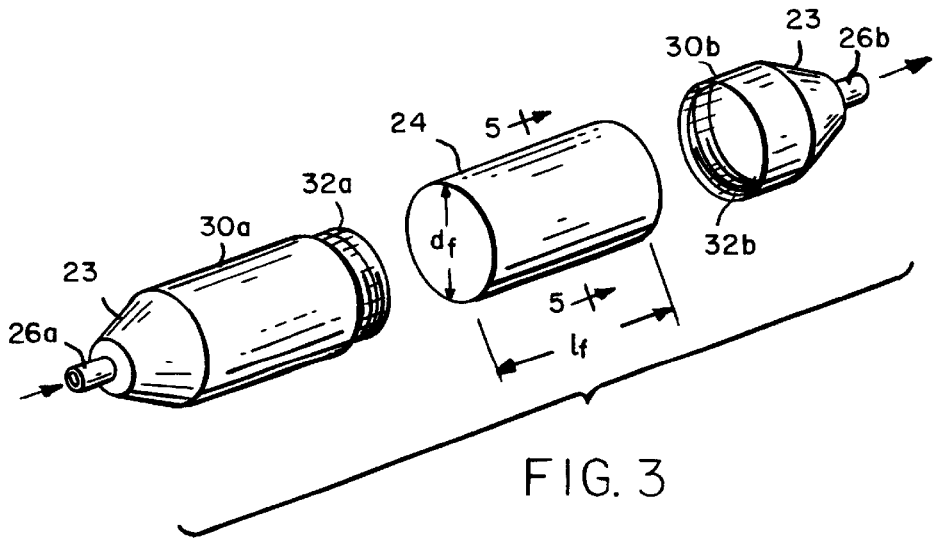
FIG. 3 is an exploded view of an in-line humidifier according to the present invention.

As further shown in FIGS. 2–3, the in-line humidifier 20 includes a housing 22, having an inlet and outlet connection 26a, b and a humidifing element 24 disposed therein. As shown in FIG. 2, housing 22 preferably includes at least an area 28 that is translucent or clear so the user can observe the condition of the humidifying element 24. Alternatively, the entire housing, or a substantial portion of the housing (60%, 70%, 80% or 90% or more of the housing surface area) may be constructed of a translucent or clear material to enable observation of humidifying element 24.

In one embodiment as shown in FIG. 2, the housing 22 forms a one-piece structure in which is disposed the humidifying element 24. In a second embodiment, as shown in FIG. 3, the housing 22 includes two subsections 30a, b that are releasably secured to each other so as to form a single housing like that shown in FIG. 2 when assembled together. In the illustrated embodiment, one subsection 30a includes a male threaded connection 32a and the other section a female threaded connection 32b to threadably secure the subsections 30a, b together. The subsections 30a, b, however, can be configured with other connecting means, e.g., press fit, etc. Preferably, the subsections 30a, b also are configured so the gas flows through the humidifying element 24 and does not escape the housing 22.

The housing's inlet connection 26a and outlet connection 26b are any one of a number of suitable connections, e.g. male/female luer lock connections or slip-on tubing connections (e.g., tubing slipped over a spigot). The inlet and outlet connections 26a, b are arranged so the gas or air flows through the humidifying element 24 in a manner best suited for releasing moisture that is retained in the humidifying element to the flowing gas. In one embodiment, the inlet connection 26a is disposed in one end cap 34 and the outlet connection 26b is disposed in the other end cap so the gas passing through the humidifier 10 flows along the long axis of a cylindrical humidifying element 24. In an alternative embodiment, the end connections 27a, b are diametrically opposed on the shell of the housing 22 as shown in phantom in FIG. 2.

Housing 22 is suitably constructed from a variety of materials. For example, plastics will be suitable, preferably rigid materials, such as a polypropylene or high-density polyethylene. Polyfluorocarbons also can be employed such as an extruded teflon housing. Stainless steel or other metal also can be employed, although may be less preferred for cost reasons. Typically, housing 22 is constructed of one or more materials that can be shipped in a sterile condition from a manufacturer to a remote facility (e.g., hospital) for later use.

Although FIGS. 2–3 illustrate the housing 22 as having a generally cylindrical structure with hemispherical end caps (FIG. 2) or truncated conical end caps (FIG. 3) this is not a limitation as the housing can have any of a number of geometrical configurations or shapes or combination of shapes. For example, the housing 22 can be configured using cylindrically shaped members that are joined at an angle to each other so as to form an L-shaped in-line humidifier. The thickness and other details of the housing 22 are established based on the humidity, pressure and flow conditions of the intended use as well as any external forces and/or external environmental conditions (e.g., in situ sterilization and impact loads).

Figure 4A:
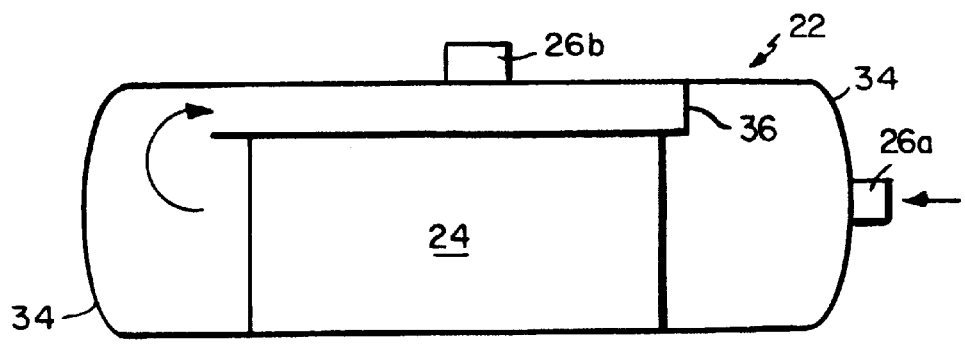
FIGS. 4A and 4B are cross-sectional side views of alternative in-line humidifier embodiments according to the present invention.
Figure 4B:
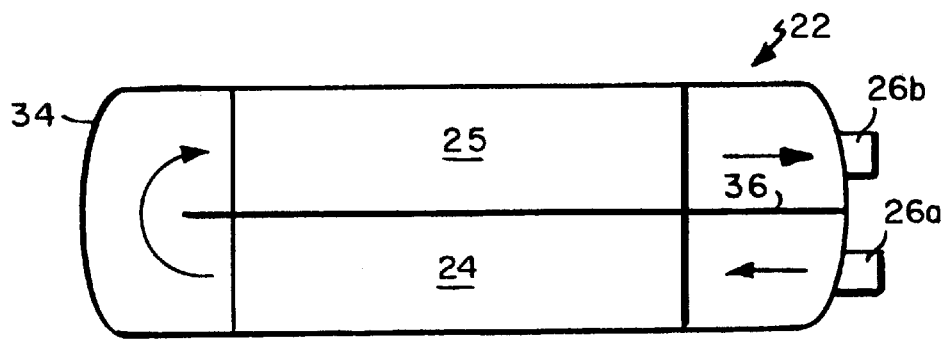

In a further aspect of the invention, as shown in FIG. 4A, housing 22 can include one or more internal baffle(s) 36 that direct gas flow through the humidifying element 24 and out of the housing. Such an arrangement allows the inlet and outlet connections 26a, b to be positioned so as to have differing orientations, e.g. positioned so one connection is an end cap 34 and the other connection in the shell of the housing (e.g., orthogonal to each other). Alternatively, the housing 22 includes one or more baffles 36 and the humidifying element 24 comprises two or more sub-sections 25a, b so the gas makes two or more passes through the humidifying element. As shown in FIG. 4B, with such a design the inlet and outlet connections 26a, b can be disposed in the same end cap 34.

The humidifying element 24 includes a material that preferably can be hydrated and which exhibits good moisture exchanging properties with a flowing gas. The humidifing element 24 also includes a support structure or capability so as to maintain the humidifying element in its desired configuration (e.g., cylindrical) and so the gas can flow therethrough and adsorb moisture from the hydrated material. As such, the humidifying element can include one or more elements to perform the above functions.

Figure 5:
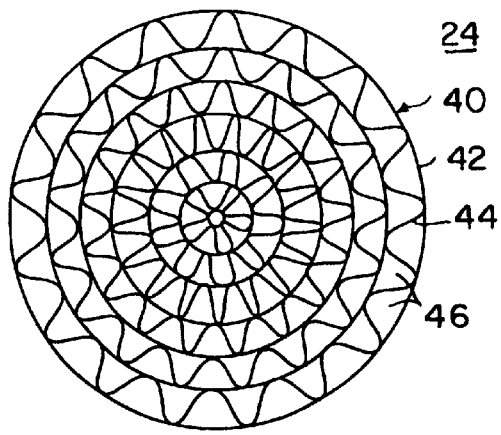
FIG. 5 is a cross sectional view of the humidifying element of FIG. 3 along line 5—5.

In an exemplary embodiment shown in FIG. 5, the humidifying element 24 includes a plurality of concentric layers 40 that are substantially parallel to the direction of flow of the gas through the housing 22 and the humidifying element 24. Each concentric layer 40 includes a plain paper sub-layer 40 having a smooth surface and a corrugated paper sub-layer 42 that preferably is attached thereto using any of a number of means known to those skilled in the art. In a more specific embodiment, the plain paper sub-layer 40 and the corrugated paper sub-layer 42 are formed as a continuous sheet and this sheet is wound about a common axis to form the plurality of concentric layers 40 shown in FIG. 5.

When so formed, the corrugated paper sub-layer defines a plurality of passages 46 that extend along the entire length of the humidifying element and which are open at both ends of the element. The corrugations also maintain sufficient structural rigidity when hydrated so the flow passages 46 remain open and the humidifying element 24 essentially maintains its structural configuration. In this way, the gas can flow along the entire length of the humidifying element 24 through the flow passages 46 and adsorb moisture from the surrounding hydrated paper of both the corrugated paper sub-layer 42 and the plain paper layer 40.

The humidifying element 24 also can be constructed from a variety of other materials. For example, the humidifying element 24 can be made of a sheet of flexible plastic foam material, preferably with one surface of which is configured so has to have a plurality of ridges and valleys extending substantially parallel to each other. The ridges and valleys may form, for example, a saw tooth pattern, a square pulse type of pattern or a sinusoidal pattern. The sheet is suitably then wound about itself along a common axis so that the ridges and valleys cooperate to form a plurality of flow passages.

In general the humidifying element 24 can be any type of reservoir that allows efficient humidification of a gas flowing therethrough. Also, while FIG. 3 depicts a preferred cylindrical shape, humidifing element 24 can be formed in a variety of other designs that would be appropriate for the specific configuration of the housing 22. For example, the humidifing element can be hexagonal or octagonal in shape. Other physical characteristics of the humidifing element 24, such as the thickness of the element are established so as to minimize flow and pressure losses, maximize available area for moisture exchange, establish the level of hydration required for use and the physical configuration of the housing.

In a further embodiment, the humidifying element 24 is treated with a germicide or other agent so as to minimize the potential for infection and the like when the flowing gas is being humidified.

Suitable dimensions of devices of the invention and the components thereof can vary rather widely and can be readily determined by those skilled in the art based on the present disclosure. In general, the device should have a shape and length so that the device is capable of being employed as an in-line humidifier during eye surgery procedures. Nevertheless, suitable dimensions include the following. The usable length of the housing 22 (length $1_h$ in FIG. 1) suitably may be from about 25 to about 50 mm and correspondingly a suitable length for the humidification element 24 (length $1_f$ in FIG. 3) maybe from about 20 to about 45 mm. Suitable diameters of the housing 22 (diameter $d_h$ in FIG. 1) may be from about 10–25 mm and suitable diameters for the humidification element 24 (diameter $d_f$ in FIG. 3) may be from about 9 to about 20 mm. Additionally, the thickness of the housing 22 can be 2 mm or more, more particularly in the range of from about 2 to about 4 mm.

The use of the humidifier 20 and system 10 of the present invention can be further understood from the following discussion relating to a method for treating a retinal tear or detachment by means of the laser photocoagulation technique and with reference to FIGS. 6A–C. Reference also shall be made to FIGS. 1–3 and 5 for specific components or elements of the in-line humidifier 20 and system 10 of the present invention not otherwise shown in FIGS. 6A–C.

In treating the retinal tear or detachment, the user (e.g. medical practitioner) prepares the in-line humidifier 20 and humidification system 10 for use. As such, the practitioner removes the in-line humidifier 20 from its sterile packaging and the humidifying element 24 therein is charged or hydrated with a liquid such as a saline solution. In a more particular embodiment, the humidifying element is hydrated with a sufficient quantity of liquid so it is saturated.

The humidifing element 24 can be charged or hydrated by alternative methods. In one technique, the nozzle of a syringe or other such instrument containing a predetermined amount of liquid is inserted through either of the inlet or outlet connection 26a, b and the liquid is injected onto the humidifying element 24. The amount of liquid to be injected and the rate of injection preferably is established so the fluid hydrates, more preferably saturates, the humidifying element 24 without spillage.

Alternatively, fluid can be added to the device without disassembly of the device or insertion through the above noted gas flow path inlet/outlets, e.g. fluid can be introduced through a resealable opening or the like in the device. More specifically, a nozzle of the syringe can be passed through a resealable port or grommet 41 in the shell or end cap 34 of the housing. As is known to those skilled in the art, a resealable grommet reseals itself when the nozzle of a syringe is withdrawn. In an exemplary embodiment, 10 ml of saline solution when injected onto a corrugated paper-humidifing element saturated the element.

In a further technique for hydrating the element 24, which is particularly applicable to a multi-piece housing (see FIG. 3), the housing 22 is disassembled by means of the threaded connection 32a, b so the humidifying element 24 can be removed from within the housing. The removed humidifying element 24 is then hydrated by placing or immersing the element in a liquid bath, e.g. a saline solution, until the element is hydrated. Alternatively, a syringe is used to inject the liquid directly onto the humidifying element 24 to hydrate it. As indicated above, the humidifying element 24 (i.e., the hydratable material comprising the element) is preferably saturated. After the element has been hydrated the humidifing element 24 is re-installed in one housing part 30a and the housing parts 30a, b are threaded together and re-secured to each other to reform the housing 20. The element 24 also can be charged or hydrated by other procedures.

After preparing the in-line humidifier 20 for use, it is interconnected to the other components of the system. For example, the female male Luer-Lok at the inlet connection 26a receives the male Luer-Lok attached to the interconnecting tubing 16 so as to establish a fluid connection between humidifier 20 and either the filter 14 or the gas supply 12. Similarly, the male Luer-Lok at the outlet connection 26b is inserted into the female Luer-Lok provided on the interconnecting tubing 16 being interconnected thereto so as to establish a fluid connection between the humidifier and the cannula 102 that is inserted into the eye 2.

In treating a retinal tear or detachment using a photocoagulation technique employing a laser, a cutting/aspirating instrument 100, a cannula 102 and a light transmitting instrument 104 are inserted through the sclera so one end of each resides intraocular. The light transmitting instrument 104 is configured so the light from the laser (not shown) can be directed to specific locations on the retina The cutting/aspirating instrument is disposed so an end thereof is proximate the retinal tear.

Initially, the vitreous gel, especially all strands causing traction on the retinal tear are removed or aspirated by means of the cutting/aspirating instrument 100. As the vitreous gel is being aspirated, the intraocular volume is maintained by a continuous infusion of a fluid, such as a balanced salt solution (BSS), through the cannula 102. Any subretinal fluid is also aspirated through the retinal tear. Thereafter, the vitreous fluid is aspirated and exchanged with a humidified gas such as air passing through the cannula 102. In the method of the present invention, the gas or air being exchanged is humidified by means of the in-line humidifier 20 and humidification system 10 as herein above-described.

The retina surrounding the tear is then repeatedly exposed to the laser light from the light transmitting instrument 104 so as to form a plurality of heat spots on the retina surrounding the retinal tear. In particular, the practitioner manipulates the light transmitting instrument 104 so that a plurality of rows of a plurality of such heat spots surrounds the retinal tear. In this way, the retinal tear is photocoagulated with a laser to achieve a thermal adhesive injury. The heat spots also produce scars that prevent fluid from passing through and collecting under the retina.

Thereafter, the intraocular gas or air, infused while exposing the retina surrounding the retinal tear to laser light, is totally exchanged for a longer-lasting gas, such as sulfur hexafluorine or perfluoro propane. This gas allows an adequate tamponade time for the therapeutic chorioretinal scar to develop. Preferably, the longer lasting gas being infused is humidified using the in-line humidifier 20 and system 10 of the present invention. After completing the "in eye" portion of the treatment procedure, the inserted instruments and cannula are removed from the eye and the spent or used in-line humidifier 20 is disposed of in accordance with normal and usual practices.

During the treatment procedure and, in particular when infusing the humidified gas into the eye, the practitioner, by visual observation through the clear area 28 of the housing 22, determines if the humidifying element 24 or humidifier should be replaced. For example, the practitioner visually observes the humidifying element 24 through the clear area 28 to see if the element appears to be dried out as a means for making such a determination. If it is determined that the humidifying element 24 is no longer sufficiently hydrated and thus is no longer capable of performing its humidifying function, then the spent in-line humidifier is replaced with a freshly charged or hydrated in-line humidifier.

For purposes of easily maintaining sterility of the field, the preferred action is to replace the spent element with a new humidifier that has been properly charged with liquid. This course of action also allows a practitioner to prepare a humidifier in advance to minimize the time amount of time required to return the humidified air supply back to service. It is within the scope of the present invention, however, to re-charge the humidifying element 24 of an in-line humidifier 20 that is in use by either injecting additional liquid onto or into the humidifying element or by re-immersing the element in a liquid bath as described above.

The invention also includes device kits that comprise an in-line humidifier 20 in an assembled configuration with or without interconnecting tubing packaged in a sterile condition. Alternatively, the humidification element 24 and housing 22 can be supplied together in the sterile packaging for later assembly by the practitioner. Preferably the in-line humidifier 20 is provided in its assembled condition.

Although a preferred embodiment of the invention has been described using specific terms, such descriptions are for illustrative purposes only, and it is to be understood that changes and variations may be made without departing from the spirit or scope of the following claims.

What is claimed is:

1. An in-line humidifier comprising:
    a housing having inlet and outlet connections, each of which is in communication with an interior of the housing through which a gas is flowed; and
    a humidifier section disposed within the interior of the housing, the humidifier section including a material having a releasably retainable liquid therein,
    wherein the humidifier section is disposed at a predetermined locus within the housing such that gas entering through the inlet connection flows into and through the humidifying section, where the flowing gas is selectively humidified by at least some of the liquid releasably retained within the material.

2. The in-line humidifier of claim 1, wherein the housing includes first and second sections that are releasably secured to each other.

3. The in-line humidifier of claim 1, wherein a portion of the housing is configured with a visual port so as to permit visual observation of the humidifier section.

4. The in-line humidifier of claim 1, wherein the material of the humidifier section is selected from the group consisting of cellulose and absorbent synthetic materials.

5. The in-line humidifier of claim 1, wherein the humidifier section is a cylindrical member having gas passages provided therein.

6. The in-line humidifier of claim 5, wherein the gas passages extend longitudinally and wherein the humidifying section is disposed within the housing so the gas from the inlet connections is presented at one end of the cylinder and so the gas exiting from the other end of the cylinder flows to the outlet connection.

7. The in-line humidifier of claim 5, wherein the humidifier is packaged in sterile form.

8. The in-line humidifier of claim 1, wherein the humidifier section includes a plurality of concentric layers that are substantially parallel to the direction of flow of the gas through the housing and humidifying element.

9. The in-line humidifier of claim 8, wherein each concentric layer includes a plurality of paper-based layers, and wherein at least two of the paper-based layers have different textures.

10. The in-line humidifier of claim 9, wherein at least a first of the paper-based layers-defines a plurality of passages.

* * * * *